United States Patent
Quintero Osorio

(10) Patent No.: US 10,729,873 B2
(45) Date of Patent: Aug. 4, 2020

(54) T-DEVICE WITH ONE-WAY VALVE, FLOW-OCCLUSION/RELEASE SYSTEM, AND PRESSURE RELEASE VALVE

(71) Applicant: FUNDACIÓN VALLE DEL LILI, Santiago de Cali (CO)

(72) Inventor: Oscar Iván Quintero Osorio, Santiago de Cali (CO)

(73) Assignee: Fundación Valle del Lili, Santiago de Cali (CO)

( * ) Notice: Subject to any disclaimer, the term of this patent is extended or adjusted under 35 U.S.C. 154(b) by 845 days.

(21) Appl. No.: 15/304,432

(22) PCT Filed: Apr. 15, 2015

(86) PCT No.: PCT/CO2015/000006
§ 371 (c)(1),
(2) Date: Oct. 14, 2016

(87) PCT Pub. No.: WO2015/158314
PCT Pub. Date: Oct. 22, 2015

(65) Prior Publication Data
US 2017/0035986 A1 Feb. 9, 2017

(30) Foreign Application Priority Data
Apr. 15, 2014 (CO) .................................. 14-081713

(51) Int. Cl.
*A61M 16/20* (2006.01)
(52) U.S. Cl.
CPC ........ *A61M 16/209* (2014.02); *A61M 16/208* (2013.01)

(58) Field of Classification Search
CPC .............. A61M 16/209; A61M 16/208; A61M 25/10186; A61M 1/0035; A61M 16/20
See application file for complete search history.

(56) References Cited

U.S. PATENT DOCUMENTS

| | | | |
|---|---|---|---|
| 4,037,595 A * | 7/1977 | Elam .................... | A61M 16/208 128/205.11 |
| 4,207,884 A | 6/1980 | Isaacson | |
| 4,436,090 A | 3/1984 | Darling | |
| 4,854,574 A | 8/1989 | Larson et al. | |
| 5,301,667 A * | 4/1994 | McGrail .............. | A61M 16/208 128/205.13 |
| 5,598,839 A * | 2/1997 | Niles ..................... | A61M 16/08 128/205.23 |
| 6,726,598 B1 | 4/2004 | Jarvis et al. | |
| 8,485,179 B1 | 7/2013 | Meyer et al. | |
| 2004/0255948 A1 * | 12/2004 | Smith .................... | A61M 16/06 128/206.15 |
| 2012/0272956 A1 * | 11/2012 | Rusher ................ | A61M 16/208 128/203.12 |

FOREIGN PATENT DOCUMENTS

| | | |
|---|---|---|
| EP | 0997168 A1 | 5/2000 |
| GB | 2278545 A | 12/1994 |
| WO | 2012038864 A2 | 3/2012 |

* cited by examiner

*Primary Examiner* — Timothy A Stanis
*Assistant Examiner* — Joanthan S Paciorek
(74) *Attorney, Agent, or Firm* — Hodgson Russ LLP

(57) ABSTRACT

Device for use in the medical field as technical pulmonary re-expansion instrument sand comprising a T-body with one-way valve, a flow occlusion/release system, and pressure release valve, for use with patients with an artificial airway, be this an orotracheal tube or tracheostomy cannula.

6 Claims, 3 Drawing Sheets

T-DEVICE WITH ONE-WAY VALVE, FLOW-OCCLUSION/RELEASE SYSTEM, AND PRESSURE RELEASE VALVE

FIELD OF THE DISCLOSURE

The present invention locates in the field of medical devices, namely within the devices for pulmonary re-expansion and flow occlusion/release and pressure release valve, to be used in patients with artificial airway.

BACKGROUND OF THE DISCLOSURE

Within the management of respiratory diseases, some patients tend to receive, as part of the treatment, the placement of an artificial airway system (whether it is an orotracheal tube or a tracheostomy cannula) which are indicated in such cases wherein having an available airway is required, whether, among other reasons, because the upper airways are obstructed or injured, or due to the health condition of the patient it is required, or to guarantee an artificial airway for some undetermined time. Upon placing the artificial airway, the physiological functions of the glottis (vocal chords) are altered, which are directly related with voice generation and ventilation; in this last process the vocal cords widen during inspiration to allow passage of air through the airways and narrow down during exhalation, which allows for a pause at the end of the inspiration, this generates positive pressure inside the lungs favoring air redistribution through the alveolar units, which improves lung ventilation, prevents and reduces atelectasis levels (lung collapse). Is due to these alterations that these types of patients, routinely, require or are benefitted by strategies that let them improve their lung capacity by means of lung re-expansion techniques.

A lung re-expansion technique is defined as any maneuver which temporarily increases alveolar pressure above normal ventilation and maintains that pressure beyond normal time. The exercises for lung re-expansion are carried out by taking sustained maximum inspirations by means of a short apnea at the end of inspiration, followed by a slow passive exhalation.

The techniques for lung re-expansion serve the purpose of effectively expanding the lungs. In order to accomplish this goal, diverse techniques are used, called lung re-expansion techniques, which can be divided in two: manual or non-instrumental techniques (techniques or commands given to the patient by the care giver or health professional) and instrumental techniques (which require the use of medical devises or instruments).

Amongst the instrumental techniques there are various devises used to generate lung re-expansion, amongst which there are: mechanical ventilators, manual resuscitators and respiratory incentives (volumetric or by flow) and others. Mechanical ventilators (such as Servo 900, Servo I, Puritan Benett, Bipap and Cpap, and others) are used to provide "non-invasive mechanical ventilation". Mechanical ventilators work under the positive pressure principle, which causes the risk of generating pressure or volume induced trauma. They work alone, in a programmed manner, but depend on electric energy or batteries. They are mainly used in the acute stages of the diseases; the patients can remain days or even weeks connected to them and as the patient improves his health condition, they are disconnected, by means of the patient's very own recovery aided, in a case basis, by the respiratory incentive or by non-instrumental techniques of lung re-expansion (verbal commands that ease the patients to hold air inside their lungs for a few seconds at the end of the inspiration).

Manual resuscitators, on their side, are self-inflatable bags used to provide positive pressure during resuscitation maneuvers, but their use is very common in patients with an artificial airway, in acute phases, since they provide all the respiratory support the patient requires. The manual resuscitator, which is costly compared with the incentive, but much cheaper in comparison to the ventilators, works under the positive pressure principle, i.e. it requires to be manipulated by someone pressing the bag so the air enters the lung, generating the risk of volume or pressure induced trauma (although some of them have a pressure release valve, which makes them more costly), they lack an occlusion system for inspired flow, because of which it makes no pause at the end of the inspiration.

The volume or flow respiratory incentives are used in patients that can breathe through the mouth. In order to couple them for a tracheotomy, the replace the nozzle placing a "T adapter with a one-way valve". The T adapter, with one-way valve is designed to make micro-nebulization in patients with an artificial airway and because of this reason they do not achieve the lung re-expansion. The respiratory incentives in patients with an artificial airway currently in existence do not make a pause at the end of the inspiration, they do not have an occlusion/release system or a pressure release valve.

There is another type of respiratory incentives which difference lays in that the latter a makeshift T is placed with a one-way valve (used for nebulization in patients with an artificial airway). But this manner of applying the technique does not allow to extend the pause at the end of the inspiration.

The T device with a one-way valve, a flow occlusion/release system, and a pressure release valve proposed in the proposed intervention makes part of the category of respiratory incentives and solves all the problems that up to this moment exist in this class of devices.

BRIEF SUMMARY OF THE DISCLOSURE

The T device with a one-way valve, flow occlusion/release system, and pressure release valve proposed in this invention allows the device's operator to control the inspiration pause time, allowing a few seconds for the patient to hold his breath favoring his alveolar recruitment. By allowing the patient's active respiration, the lung is inflated by means of physiological respiration which minimizes the risk of pressure induced trauma (lesions caused by elevated pressure) or volume induced trauma (lesions cause by elevated volumes).

The one-way valve of the T device with one-way valve, flow occlusion/release system, and pressure release valve proposed by tis invention is located at the largest diameter of the device which reduces the resistance level of the inspired air and comprises a plastic membrane allowing entrance of air and prevents the air returning back. The one-way valve also allows the connection with other systems such as, for example, lung parameters measuring devices, oxygen support and respiratory incentives, and others.

The flow occlusion/release system of the T device with one-way valve, flow occlusion/release system, and pressure release valve proposed by this invention is comprised of a lid, some windows and a retaining system. Its function consists of isolating the patient's airway from the outside environment when making the respiratory pause preventing contamination by manipulation. The air exit windows favor, also, slow and prolonged expiration, which prevents lung collapse and favor lung re-expansion, increasing, also, residual functional capacity. This system also allows to extended respiratory pause, easing in-lung air distribution.

The flow occlusion/release system comprises a mobility that allows the user to control the manner in which the inspiration pause can be shortened according to his or her own needs.

The retaining system of the flow occlusion/release system prevents the lid of the flow occlusion/release system to come off the device due to the pressure inside the lung. The pressure release valve of the T device with one-way valve, flow occlusion/release system, and pressure release valve proposed in this invention constitutes a safety system that activates if there is an increase in the inner lung pressure when the occlusion/release system's lid is being restrained. The pressure release valve prevents pressure increments of the pressure inside the lungs in case the patient wishes to cough and the lid of the flow occlusion/release system has not been released. The release valve comprises a spring that allows for the lid to remain closed, or open for the air to exit through the orifices in case there is an increase in pressure.

It comprises, also, a cone shaped inner chamber which purpose is to reduce the dead space and favor laminar flow.

Both the one-way valve and the flow occlusion/release system and the pressure release valve can be disassembled to allow the internal cleaning of the device.

DESCRIPTION OF THE DRAWINGS

In order to complete the description being made and with the purpose of aiding in a better understanding of the characteristics of the invention, the present specification is accompanied as an integral part thereof, the set of drawings in which, with illustrative and non-limitative purposes, the following has been presented.

Figure 1:
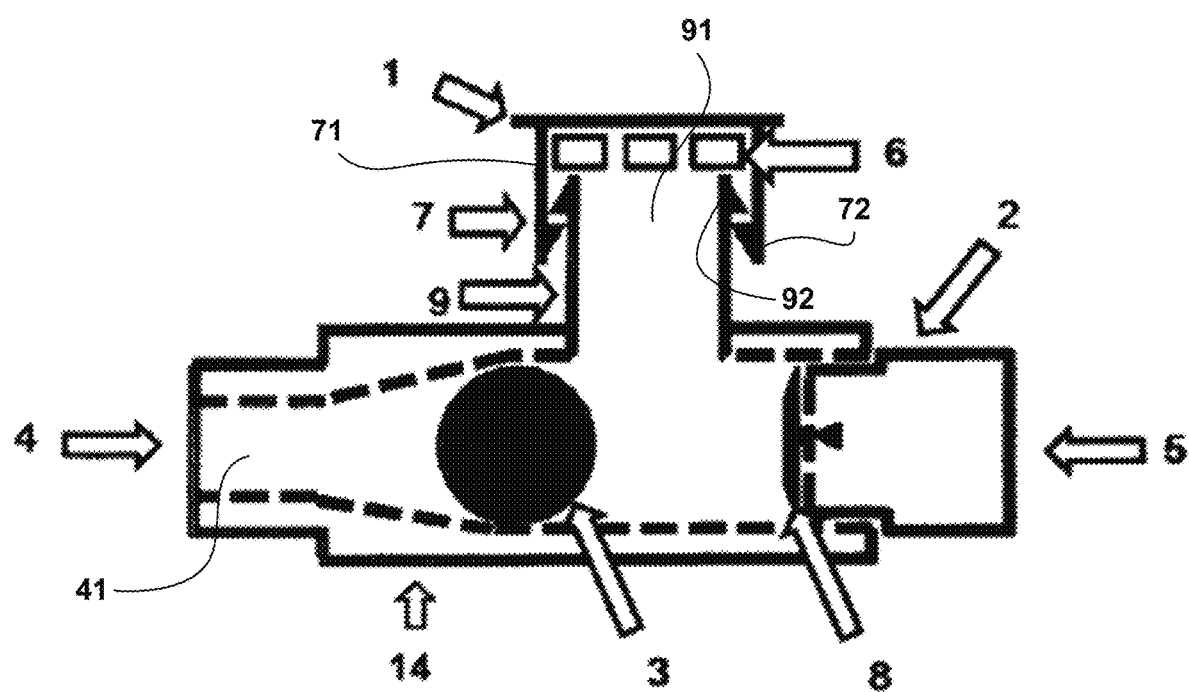
FIG. 1 shows.
Figure 2:
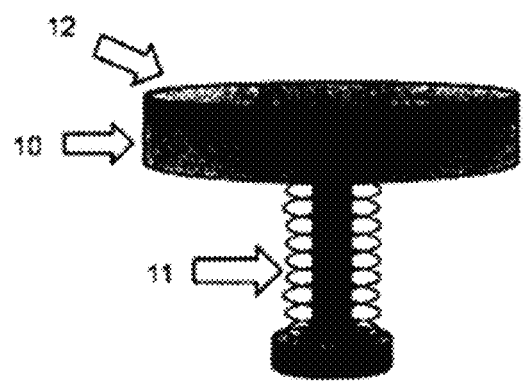
Figure 3:
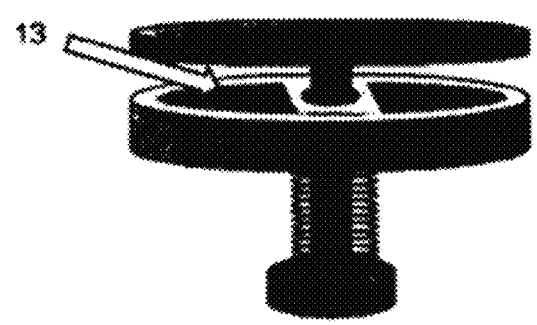
Figure 4:
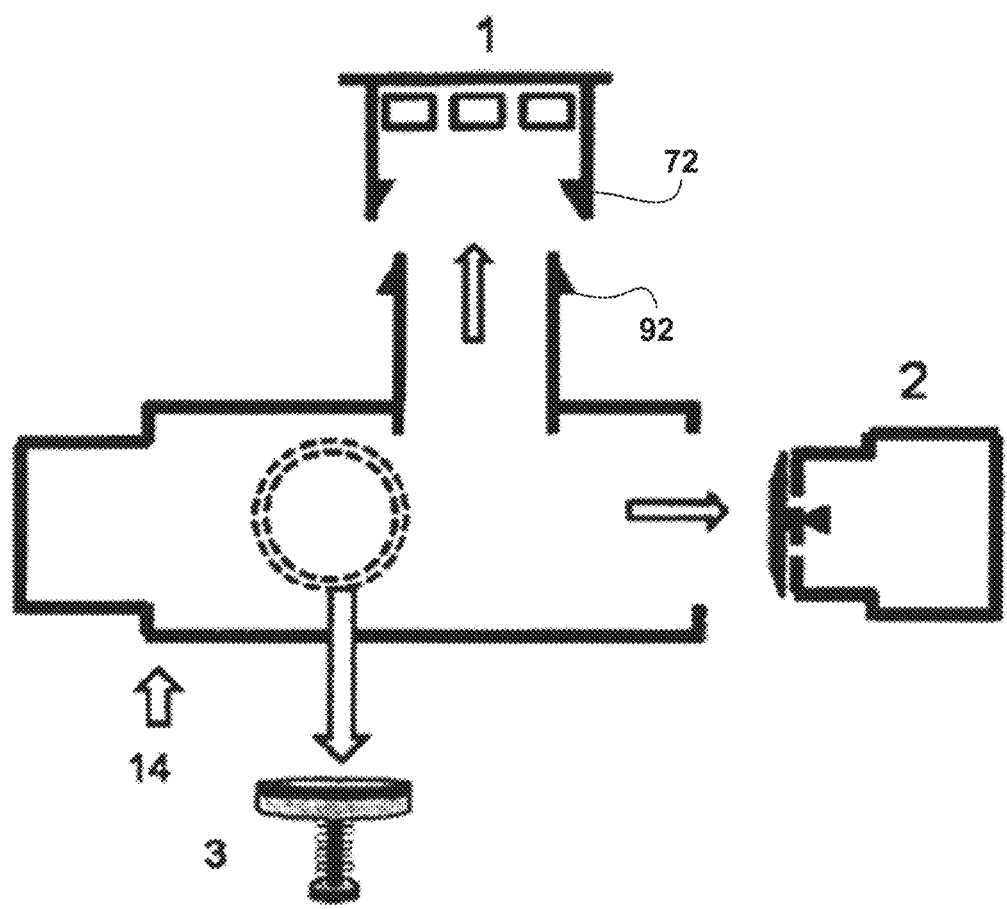

A T body to which the lid (1), configured as a flow/occlusion release system, the one-way valve (2), the pressure release valve (3), the base element (14) are attached has a proximal end (4) and intermediate end (9). The proximal end (4) includes a proximal channel (41), and the intermediate end (9) includes an intermediate channel (91) disposed orthogonally and radially from the proximal channel (41).

The lid (1) has, also, a retaining system (7) comprising a receiver (71) having a plurality of windows (6), The receiver (71) is configured to fit with the intermediate end (9). The retaining system (7) further comprises a male fit end (92) disposed on the intermediate end (9) and a female fit end (72) disposed on the receiver (71).

The one-way valve (2) has a distal end (5) and a plastic membrane (8).

FIG. 2 shows:

The pressure release valve (3) and in it is possible to see a body (10), a spring (11) and a T system (12).

FIG. 3 shows:

The pressure release valve (3) in an open state such that orifices (13) are visible.

FIG. 4 shows:

The flow lid (1), the one direction valve (2) and the pressure release valve (3) disassembled from the base element (14).

DETAILED DESCRIPTION OF THE DISCLOSURE

To clearly show the nature and scope of the advantageous application of the T device with a one-way valve, flow occlusion/release system, and pressure release valve constituting the object of this invention next are described their structure and function making reference to the drawings which because they present a preferred embodiment of said object, in an informative way, should be regarded in their broader sense and not as limiting the application and content of the invention. The working of the T device with one-way valve, flow occlusion/release system, and pressure release valve constituting the object of the invention is achieved in the following way:

First the proximal end (4) must be coupled to the artificial airway or tracheotomy cannula of the patient. Then, the lid (1) of the flow occlusion/release system must be pressed, such that the air entering through the distal end (5) remains held inside the lung; the one-way valve (2), by means of membrane (8), allows passage of air and simultaneously prevents it from leaving. Once the patient has achieved his or hers full lung capacity, a few seconds must be counted which favors a greater lung re-expansion.

Then the finger must be withdrawn from the lid (1), and by the positive pressure inside the lung the lid rises and air exists through the windows (6). Repeating this action according to the protocol of the institution or criteria of the care giver or health professional carrying out the intervention, (according to the specific needs of the patient).

Finally, the lung re-expansion device is removed from the tracheotomy cannula.

As a security system, if the patient coughs when the lid (1) is being restrained, the pressure increase being generated activates the pressure release valve (3) allowing the exit of a certain amount of air, this preventing a lesion induced by pressure (which happens in case of elevated pressures).

The invention claimed is:

1. A device used as an instrumental technique for lung re-expansion comprising:
    a T-shaped body including:
        a proximal end (4) including a proximate channel (41); and
        an intermediate end (9) including an intermediate channel (91) disposed orthogonally and radially from the proximal channel (41);
        wherein the T-shaped body includes:
            a lid (1), configured as a flow occlusion/release system, disposed in line with the intermediate channel (91) at the intermediate end (9), the lid (1) comprising a retaining system (7) including a receiver (71) having a plurality of windows (6), the receiver (71) configured to fit with the intermediate end (9);
            a one-way valve (2) disposed in line with the proximal channel (41) at an end opposite to the proximal end (4), the one-way valve (2) comprising a membrane (8) configured to permit air passage into the T-shaped body while preventing air passage out of the T-shaped body, and
            a pressure release valve (3) disposed in line with the proximal channel (41) at the proximal end (4), the pressure release valve (3) configured to release sufficient air to mitigate an overpressure within T-shaped body.

2. The device to be used as an instrumental technique for lung re-expansion according to claim 1, wherein the windows (6) are configured to permit passage of air sent by a lung.

3. The device to be used as an instrumental technique for lung re-expansion according to claim 1, wherein the retaining system (7) further comprises a male end (92) disposed on the intermediate end (9) and a female end (72) disposed on the receiver (71).

4. The device to be used as an instrumental technique for lung re-expansion according to claim 1, further comprising orifices (13) and a pressure release valve consisting of a spring (11) which is configured to keep a lid of the pressure release valve (12) closed.

5. The device to be used as an instrumental technique for lung re-expansion according to claim 1, further comprising a one-way valve (2) located at a largest diameter of the device and a plastic membrane (8).

6. The device to be used as an instrumental technique for lung re-expansion according to claim 1, wherein the one way valve (2) and the pressure release valve (3) are configured to be disassembled thereby easing disinfection of the device.

* * * * *